United States Patent
Benn

(10) Patent No.: US 9,737,356 B2
(45) Date of Patent: Aug. 22, 2017

(54) ELECTROSURGICAL INSTRUMENT AND SYSTEM

(71) Applicant: GYRUS MEDICAL LIMITED, Cardiff (GB)

(72) Inventor: Christopher Charles Benn, Bristol (GB)

(73) Assignee: GYRUS MEDICAL LIMITED, Cardiff (GB)

(*) Notice: Subject to any disclaimer, the term of this patent is extended or adjusted under 35 U.S.C. 154(b) by 297 days.

(21) Appl. No.: 14/281,164

(22) Filed: May 19, 2014

(65) Prior Publication Data

US 2014/0343548 A1 Nov. 20, 2014

(30) Foreign Application Priority Data

May 17, 2013 (GB) .................... 1308904.0

(51) Int. Cl.
*A61B 18/14* (2006.01)
*A61B 18/00* (2006.01)
*A61B 18/16* (2006.01)

(52) U.S. Cl.
CPC ...... *A61B 18/1402* (2013.01); *A61B 2018/00577* (2013.01); *A61B 2018/00601* (2013.01); *A61B 2018/00625* (2013.01); *A61B 2018/1412* (2013.01); *A61B 2018/162* (2013.01); *A61B 2218/008* (2013.01); *Y10T 29/49117* (2015.01)

(58) Field of Classification Search
CPC .......... A61B 18/1402; A61B 18/1492; A61B 18/1485; A61B 2018/00577; A61B 2018/1475; A61B 2018/00595; A61B 2018/00589; A61B 2018/00601; A61B 2018/126; A61B 2218/008
See application file for complete search history.

(56) References Cited

U.S. PATENT DOCUMENTS

| 5,401,274 | A | * | 3/1995 | Kusunoki | A61B 18/1482 606/41 |
| 5,968,042 | A | * | 10/1999 | Ernster | A61B 18/1402 604/21 |
| 6,210,405 | B1 | | 4/2001 | Goble et al. | |
| 6,458,126 | B1 | | 10/2002 | Doyle | |
| 6,482,202 | B1 | | 11/2002 | Goble et al. | |

(Continued)

OTHER PUBLICATIONS

Nov. 15, 2013 British Search Report issued in British Application No. 1308904.0.

(Continued)

*Primary Examiner* — Michael Peffley
(74) *Attorney, Agent, or Firm* — Oliff PLC

(57) ABSTRACT

An electrosurgical instrument includes an instrument shaft, and a suction tube extending along the shaft, the suction tube being formed of an electrically-conductive material and including a way or portion by which it can be connected to a source of electrosurgical energy. A blade-like tissue treatment electrode extends from the shaft, the blade-like tissue treatment electrode being integrally formed by the distal end of the suction tube. The distal end of the suction tube is flattened to form the blade-like tissue treatment electrode, and the distal end of the suction tube is disposed at an angle to the longitudinal axis of the shaft.

17 Claims, 2 Drawing Sheets

(56) References Cited

U.S. PATENT DOCUMENTS

| | | | |
|---|---|---|---|
| 7,169,148 B2 * | 1/2007 | O'Halloran | A61B 18/1485 606/49 |
| 7,481,807 B2 * | 1/2009 | Knudsen | A61B 18/148 606/41 |
| 7,666,186 B2 * | 2/2010 | Harp | A61B 17/1624 606/85 |
| 8,992,520 B2 † | 3/2015 | Van Wyk | |
| 2004/0024401 A1 * | 2/2004 | Garito | A61B 18/1402 606/45 |
| 2005/0273097 A1 * | 12/2005 | Ryan | A61B 18/1402 606/45 |
| 2013/0041363 A1 * | 2/2013 | Van Wyk | A61B 18/1402 606/33 |

OTHER PUBLICATIONS

Jun. 7, 2017 Office Action issued in Chinese Patent Application No. 201410252444.4.

\* cited by examiner
† cited by third party

ELECTROSURGICAL INSTRUMENT AND SYSTEM

TECHNICAL FIELD

Embodiments of the invention relate to an electrosurgical instrument and/or to an electrosurgical system for the treatment of tissue. Such systems are commonly used for the vaporisation and/or coagulation of tissue in surgical intervention, most commonly in "keyhole" or minimally invasive surgery, but also in "open" surgery.

BACKGROUND TO THE INVENTION AND PRIOR ART

There is a frequent requirement during a surgical procedure for suction in order to remove matter from the surgical site, whether it is tissue debris, smoke, fluid, gas bubbles or other unwanted matter that interfere with the procedure or obscure the surgeon's view of the surgical site. U.S. Pat. Nos. 6,210,405 & 6,482,202 describe examples of this type of surgical instrument. In addition, U.S. Pat. No. 6,458,126 describes a further example wherein a combined cutter and coagulator element is formed by bending a suction tube to a desired angle followed by pressing or compressing the conductive wall of the tube together and removing a portion of insulation therefrom.

SUMMARY OF THE INVENTION

Embodiments of the invention provide an electrosurgical instrument having a tubular shaft along which a suction lumen is provided. The shaft is electrically conductive, and is flattened at the distal end to provide an elongate tissue treatment electrode, the flattening occurring by compressing or otherwise forming the opposite sides of the tubular shaft so that they come together to form a blade-like structure. However, in order to provide for suction openings the opposite sides of the tubular shaft are not formed or brought together along the entire width of the blade-like structure, and instead one or more sections of the opposite sides remain separated in the end or edge of the blade-like structure, thereby forming openings in the end or edge of the blade-like structure that are in fluid communication with the suction lumen. With such an arrangement an electrosurgical instrument is conveniently formed with suction apertures in communication with a suction lumen integral therewith.

Accordingly, from one aspect an electrosurgical instrument is provided for the treatment of tissue, the instrument comprising a) an instrument shaft, b) a suction tube extending along the shaft, the suction tube being formed of an electrically-conductive material and including means by which it can be connected to a source of electrosurgical energy, the suction tube forming a suction lumen and c) a blade-like tissue treatment electrode extending from the shaft, the blade-like tissue treatment electrode being integrally formed by the distal end of the suction tube, and ending in a distal extremity, the distal extremity having one or more openings in communication with the suction lumen.

The formation of the end of the suction tube into a blade-like tissue treatment electrode avoids the need for a separate electrode element to be attached to the end of the suction tube. The fact that the suction tube already has a suction lumen running therethrough means that the tissue treatment electrode is provided with a ready-made suction lumen, thereby avoiding the problem of how to provide a suction lumen in a separate tissue treatment electrode.

Conveniently the suction tube has a generally circular cross-section. Preferably, at least a part of the distal end of the suction tube is flattened to form the blade-like tissue treatment electrode. Such a blade-like electrode is preferred for electrosurgical cutting, in stark contrast to suction coagulators that use an electrically active suction tube for tissue coagulation.

The distal end of the suction tube preferably includes one or more closed portions where the walls of the suction tube are crimped together in abutment one against another. Conveniently, the distal end of the suction tube also includes one or more open portions where the walls of the suction tube are not in abutment one against another thereby forming the one or more openings therebetween. The distal end of the suction tube typically includes one closed portion and two open portions, conceivably a central closed portion surrounded on each side by an open portion. In this way, the closed portion provides a narrow cutting blade, while the open portions provide suction lumens for the removal of tissue debris, smoke, fluid, gas bubbles or other unwanted matter.

According to one convenient arrangement, the distal end of the suction tube is disposed at an angle to the longitudinal axis of the shaft. Preferably, the angle to the longitudinal axis is in the form of a pitch angle. Using terminology common in the aircraft industry, an aircraft flying in a straight line will be subject to three types of movement, namely pitch, roll & yaw. The pitch is when the aircraft's nose tilts up or down. The aircraft rolls when the body rotates with one wing moving higher than the other. Finally, the aircraft yaws when the longitudinal direction changes, with the aircraft rotating about its midpoint. For the electrosurgical instrument of the present invention, the distal end of the suction tube is angled "upwardly" (or "downwardly"), in the sense of the pitch angle as described above.

The angle to the longitudinal axis is conveniently between 30 and 60 degrees, typically substantially 45 degrees. This allows for a blade-like electrode to be deployed at an angle from the shaft of the instrument, useful when the surgeon wishes to treat tissue to the side of the axis by which the surgical site has been accessed. This is typically the case when tissue is being treated in the region of the hip, or in other arthroscopic procedures such as the knee or shoulder. Whichever arrangement is employed, the tissue treatment electrode can be described as substantially chisel-shaped.

Another aspect of the present invention provides a method of forming a tissue treatment electrode for the treatment of tissue, comprising the steps of a) forming an annular suction tube with an open distal end, the suction tube being formed of electrically conductive material, and b) deforming the end of the suction tube into a blade-like tissue treatment section while maintaining the distal end at least partly open so as to form one or more suction apertures.

The deforming step preferably includes crimping the end of the suction tube into a flattened structure. Other arrangements, such as those involving open and closed portions are possible, as have previously been described. The deforming step conveniently also includes bending the end of the suction tube to lie at an angle to the longitudinal axis of the suction tube, again as previously described.

Embodiments of the invention further reside in an electrosurgical system for the treatment of tissue, the system comprising an electrosurgical generator and an electrosurgical instrument, the instrument including a) an instrument shaft, b) a suction tube formed of an electrically-conductive material and extending along the shaft to emerge from the distal end of the shaft to form a tissue treatment electrode, c) a first connection for connecting the suction tube to the electrosurgical generator, d) a return electrode carried by the shaft, e) a second connection for connecting the return electrode to the electrosurgical generator, and f) an insulating member spacing apart the return electrode from the suction tube, wherein in use the electrosurgical generator supplies tissue-cutting electrosurgical energy between the suction tube and the return electrode such the electrosurgical instrument is capable of the vaporisation of tissue adjacent the tissue treatment electrode.

This use of an energised suction tube to treat tissue is common with so called suction coagulators, but these instruments are only used to perform the coagulation of tissue. Where any such instruments also perform the cutting or vaporisation of tissue, a separate tissue-cutting electrode is normally provided. Embodiments of the present invention perform the cutting or vaporisation of tissue, directly using the end of the suction tube, something which has not previously been considered practicable due to the inappropriate shape of the end of the suction tube.

Another aspect of the invention provides an electrosurgical instrument having a tubular shaft along which a suction lumen is provided, the shaft being electrically conductive, and flattened at the distal end thereof to provide an elongate tissue treatment electrode, the flattening occurring by compressing or otherwise forming the opposite sides of the tubular shaft so that they lie together along at least one first portion thereof, at least two second portions of the opposite sides of the tubular shaft either side of the at least one first portion remaining separated, thereby forming at least two openings in the end or edge of the elongate tissue treatment electrode that are in fluid communication with the suction lumen.

In one embodiment the tubular shaft is angled at the distal end thereof such that the elongate tissue treatment electrode extends at an angle to the remainder of the tubular shaft. For example, the angle may be between 30 and 60 degrees.

In further embodiments, one or more additional first portions may be provided along the flattened end of the tubular shaft, separated from the other first portions by second portions that remain separated to provide suction lumens. In preferred embodiments the first portions are conveniently formed by crimping the opposite sides of the tubular shaft together.

DESCRIPTION OF THE DRAWINGS

Embodiments of the invention will now be further described, by way of example only, with reference to the accompanying drawings, in which.

DESCRIPTION OF THE EMBODIMENTS

Figure 1:
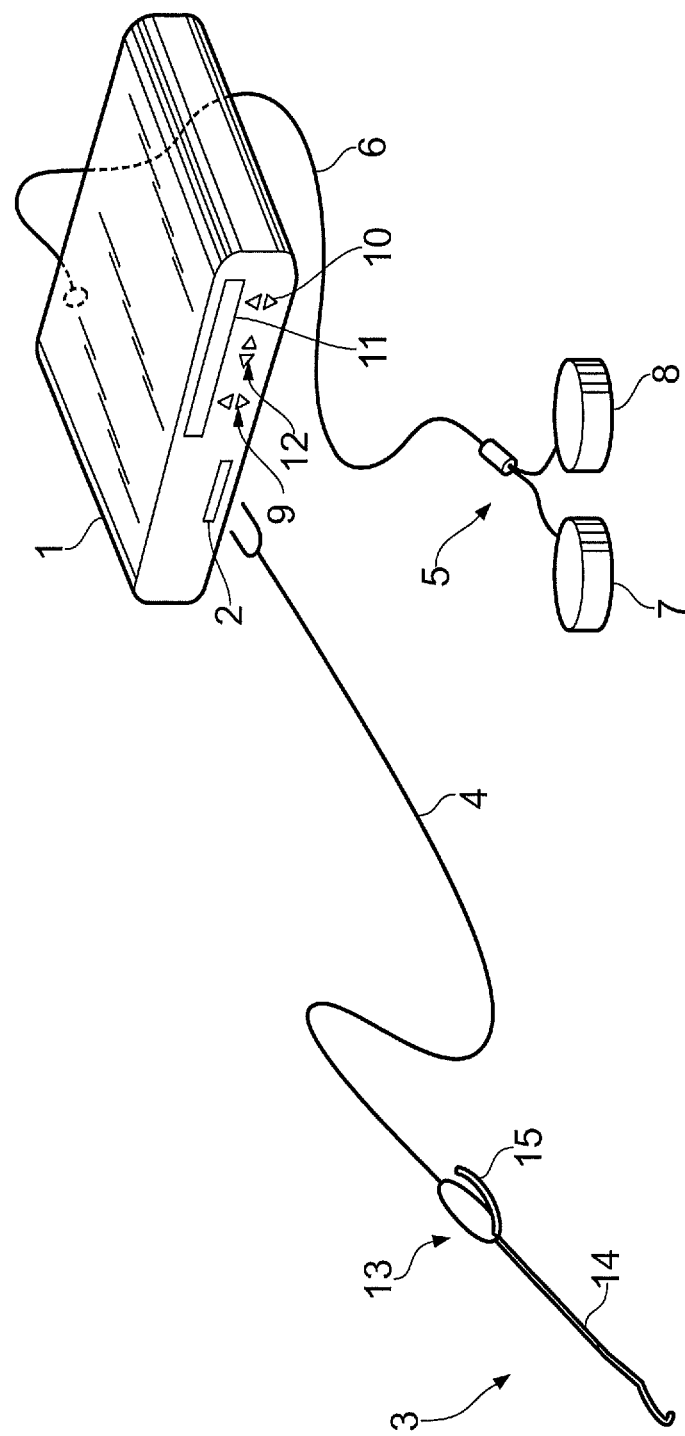
FIG. 1 is a schematic diagram of an electrosurgical system using an electrosurgical instrument in accordance with an embodiment of the present invention.

Referring to the drawings, FIG. 1 shows electrosurgical apparatus including a generator 1 having an output socket 2 providing a radio frequency (RF) output, via a connection cord 4, for an electrosurgical instrument 3. Activation of the generator 1 may be performed from the instrument 3 via a handswitch (not shown) on the instrument 3, or by means of a footswitch unit 5 connected separately to the rear of the generator 1 by a footswitch connection cord 6. In the illustrated embodiment, the footswitch unit 5 has two footswitches 7 and 8 for selecting a desiccation mode and a vaporisation mode of the generator 1 respectively. The generator front panel has push buttons 9 and 10 for respectively setting desiccation and vaporisation power levels, which are indicated in a display 11. Push buttons 12 are provided as an alternative means for selection between the desiccation and vaporisation modes.

The electrosurgical instrument 3 comprises a housing 13 with an elongate shaft 14, and tissue treatment electrodes at the distal end of the shaft, as will be described below. A movable handle 15 associated with the housing can be actuated to cause the shaft to bend. This instrument is particularly suited to the treatment of the hip joint, where a relatively long shaft with articulation capability is needed to access the area to the treated.

Figure 2:
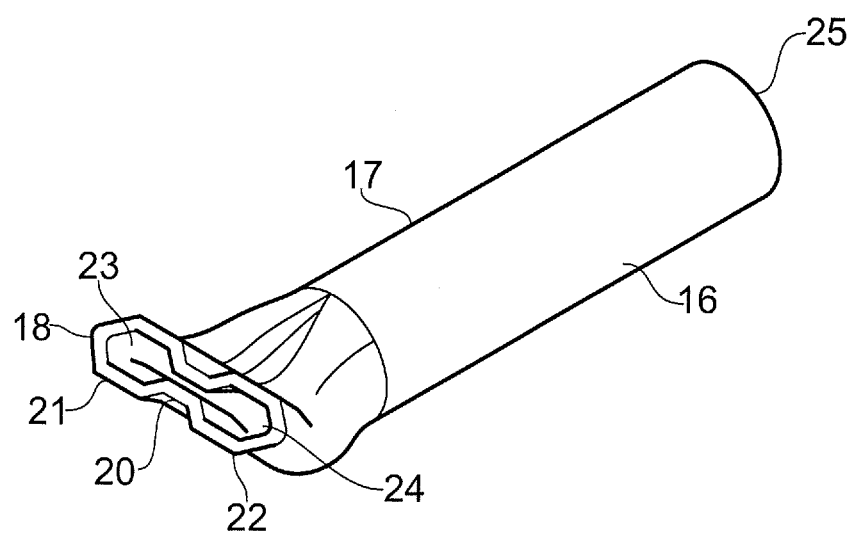
FIG. 2 is a perspective view of the suction tube of an electrosurgical instrument in accordance with an embodiment of the present invention and capable of being used in the system of FIG. 1.

FIG. 2 shows a suction tube 16 comprising a body portion 17 and a blade portion 18. The blade portion 18 extends forwardly from the body portion 17 in the form of a chisel. The blade portion 18 extends upwardly with respect to the longitudinal axis of the suction tube by an angle of approximately 45 degrees, although in other embodiments different angles may be used, for example from 30 to 60 degrees, or in yet further embodiments the blade portion need not be angled at all. The blade portion 18 is formed by crimping the end of the body portion into a flattened shape consisting of a central closed portion 20 and outer open portions 21 & 22. In the closed portion 20, the opposite walls of the suction tube are in abutment one against another so as to form as narrow a structure as possible. In the open portions 21 & 22, while the walls of the suction tube are compressed towards one another, they do not abut one another leaving suction apertures 23 & 24 therebetween. These suction apertures 23 & 24 communicate with a central suction lumen 25 defined by the suction tube 16.

Figure 3:
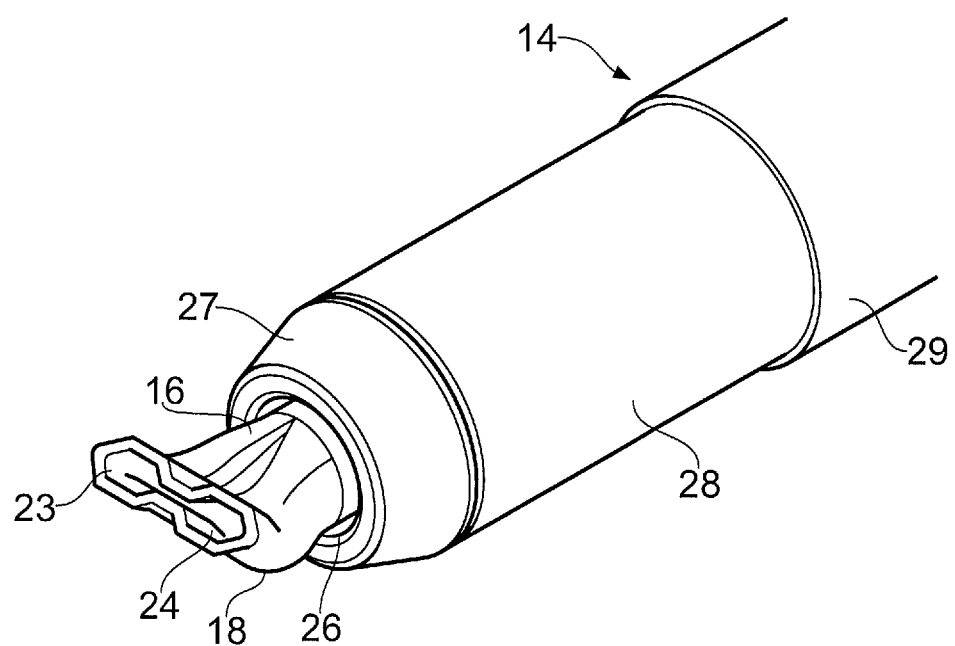
FIG. 3 is a perspective view of an electrosurgical instrument in accordance with an embodiment of the present invention and capable of being used in the system of FIG. 1.

FIG. 3 shows how the suction tube 16 is received within the electrosurgical instrument 3 as a whole. The suction tube 16 is housed within the shaft 14 of the instrument, and extends through a circular aperture 26 in an insulating ring 27. The insulating ring separates the exposed end of the suction tube from a return electrode 28, also mounted on the shaft 14. The return electrode 28 is in the form of a metallic sleeve, which is itself partially covered by an insulating sheath 29, which extends proximally for the remainder of the shaft.

In use, the instrument 3 is connected to the generator 1, and also to a source of suction (not shown). The tip of the instrument is introduced to a surgical site with tissue to be treated, and a conductive fluid is provided to surround the tip of the instrument. When the electrosurgical generator is activated, an electrosurgical RF waveform is provided to the instrument, and electric current flows between the blade portion 18 and the return electrode 28. Tissue adjacent the blade portion 18 is vaporised by the electric current and removed from the surgical site. Suction applied to the instrument 3 is such that tissue, debris, smoke, fluid, gas bubbles or other unwanted matter is evacuated from the surgical site through the apertures 23 & 24 and the suction lumen 25 in the suction tube 16.

The instrument 3 is primarily designed to be operated in a conductive fluid such as saline, with the fluid completing the circuit between the electrodes. However, the instrument 3 can also be used as a dry-field instrument, in which case the user must ensure that the electrodes are placed in contact with the tissue to be treated. The instrument 3 can also be used as a monopolar instrument, with a remote patient plate taking the place of the return electrode 28.

Alternative embodiments will be envisaged by those skilled in the art without departing from the scope of the present invention. For example, the number and orientation of the apertures described above can be varied depending on the required electrode geometry. However, more generally embodiments of the invention provide for the provision of a blade-like electrode integrally formed from the distal end of a suction tube, and also the use of a suction tube as an electrode for the electrosurgical excision of tissue, regardless of the precise embodiment used to put this into practice.

The invention claimed is:

1. An electrosurgical instrument for the treatment of tissue, the instrument comprising
    a) an instrument shaft,
    b) a suction tube extending along the shaft, the suction tube being formed of an electrically-conductive material and including means by which it can be connected to a source of electrosurgical energy, the suction tube forming a suction lumen therein, and
    c) a blade-like tissue treatment electrode extending from the shaft, the blade-like tissue treatment electrode being integrally formed by a distal end of the suction tube, and ending in a distal-most end, the distal-most end having one or more openings in communication with the suction lumen,
    wherein
    at least a part of the distal end of the suction tube is flattened to form the blade-like tissue treatment electrode, and
    the distal-most end of the suction tube includes one or more closed portions where the walls of the suction tube are crimped together in abutment one against another.

2. An electrosurgical instrument according to claim 1, wherein the suction tube has a generally circular cross-section.

3. An electrosurgical instrument according to claim 1, wherein the distal-most end of the suction tube includes one or more open portions where the walls of the suction tube are not in abutment one against another thereby forming the one or more openings therebetween.

4. An electrosurgical instrument according to claim 1, wherein the distal-most end of the suction tube includes one closed portion and two open portions.

5. An electrosurgical instrument according to claim 1, wherein the distal-most end of the suction tube includes a central closed portion surrounded on each side by an open portion.

6. An electrosurgical instrument according to claim 1, wherein the distal end of the suction tube is disposed at an angle to the longitudinal axis of the shaft.

7. An electrosurgical instrument according to claim 6, wherein the angle to the longitudinal axis is in the form of a pitch angle.

8. An electrosurgical instrument according to claim 7, wherein the angle to the longitudinal axis is between 30 and 60 degrees.

9. An electrosurgical instrument according to claim 8, wherein the angle to the longitudinal axis is substantially 45 degrees.

10. An electrosurgical instrument according to claim 1, wherein the tissue treatment electrode is substantially chisel-shaped.

11. A method of forming a tissue treatment electrode for the treatment of tissue, comprising
    a) forming an annular suction tube with an open distal end, the suction tube being formed of electrically conductive material, and
    b) crimping the end of the suction tube into a flattened structure to form a blade-like tissue treatment section with one or more closed portions where the walls of the suction tube are crimped together in abutment one against another, while maintaining a distal-most end at least partly open so as to form one or more suction apertures.

12. A method according to claim 11, further comprising bending the end of the suction tube to lie at an angle to the longitudinal axis of the suction tube.

13. An electrosurgical instrument having a tubular shaft along which a suction lumen is provided, the shaft being electrically conductive, and flattened at a distal end thereof to provide an elongate tissue treatment electrode, the flattening including compressing or otherwise forming the opposite sides of the tubular shaft so that they lie together along at least one first portion thereof, at least two second portions of the opposite sides of the tubular shaft remaining separated, thereby forming at least two openings in a distal-most end or edge of the elongate tissue treatment electrode that are in fluid communication with the suction lumen.

14. An electrosurgical instrument according to claim 13, the tubular shaft being angled at the distal end thereof such that the elongate tissue treatment electrode extends at an angle to the remainder of the tubular shaft.

15. An electrosurgical instrument according to claim 14, wherein the angle is between 30 and 60 degrees.

16. An electrosurgical instrument according to claim 13, wherein one or more additional first portions are provided along the flattened end of the tubular shaft, separated from the other first portions by second portions that remain separated to provide suction lumens.

17. An electrosurgical instrument according to claim 13, wherein the one or more first portions are conveniently formed by crimping the opposite sides of the tubular shaft together.

* * * * *